United States Patent [19]

Melvin, Jr. et al.

[11] 4,454,144
[45] Jun. 12, 1984

[54] SUBSTITUTED DIBENZO[B,D]PYRAN ANALGESICS

[75] Inventors: Lawrence S. Melvin, Jr., Ledyard; Michael R. Johnson, Gales Ferry, both of Conn.

[73] Assignee: Pfizer Inc., New York, N.Y.

[21] Appl. No.: 390,418

[22] Filed: Jun. 21, 1982

[51] Int. Cl.³ ............... A61K 31/35; A61K 31/44; C07D 311/78; C07D 405/02
[52] U.S. Cl. .................... 424/263; 549/391; 546/196; 546/269; 424/283; 424/267
[58] Field of Search ............... 549/391; 546/196, 269; 424/283, 263, 267

[56] References Cited

U.S. PATENT DOCUMENTS

| | | | |
|---|---|---|---|
| 3,507,885 | 4/1970 | Fahrenholtz | 260/345.3 |
| 3,636,058 | 1/1972 | Fahrenholtz | 260/343.2 |
| 3,856,821 | 12/1974 | Loev | 260/345.3 |
| 3,886,184 | 5/1975 | Matsumoto et al. | 260/345.3 |
| 3,901,926 | 8/1975 | Winn et al. | 260/345.3 |
| 3,968,125 | 7/1976 | Archer | 260/345.3 |
| 4,049,653 | 9/1977 | Winn | 544/150 |
| 4,118,559 | 10/1978 | Johnson et al. | 542/432 |
| 4,133,819 | 1/1979 | Johnson | 260/345.3 |
| 4,143,139 | 3/1979 | Bindra | 424/248.55 |

OTHER PUBLICATIONS

Y.-H. Wu et al., "Pyrrolidines, VII, 3-Hydroxy-1-Pyrrolidine-Carboxylic Acid Esters, *J. Medical & Pharm. Chem.*, 5, 752-762 (1962).
W. Q. Beard, Jr., et al., "Ortho Substitution Rearrangement of Certain 3-Substituted and 3,5-Disubstituted Benzyltrimethylammonium Ions by Sodium Amide," *J. Organic Chem.*, 26, 2310-2316 (1961).
G. Woolfe et al., "The Evaluation of the Analgesic Action of Pethidine Hydrochloride (Demerol)," *J. Pharmacol. Exp. Ther.*, 80, 300-307 (1944).
S. S. Tenen, "Antagonism of the Analgesic Effect of Morphine and Other Drugs by p-Chlorophenylalanine, A Serotonin Depletor," *Psychopharmacologia*, 12, 278-285 (1968).
London et al., "Suppression of Cancer Chemotheraphy-Induced Vomiting in the Cat by Nabilone, a Synthetic Cannabinoid," *Proceedings of the Society of Experimental Biology & Medicine*, 160, 437-440 (1979).
Niemegeers et al., "The Castor-Oil Test in Rats," in W.

Van Bever et al., *Synthetic Antidiarrheal Drugs*, 7, 68-73, Marcel Dekker, Inc., N.Y. 1976.

*Primary Examiner*—Nicky Chan
*Attorney, Agent, or Firm*—Charles J. Knuth; Peter C. Richardson; Allen Bloom

[57] ABSTRACT

The present invention comprises novel compounds of formula

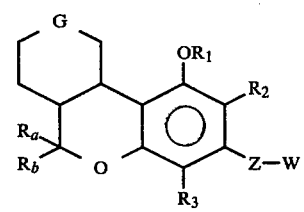

or a pharmaceutically acceptable salt thereof wherein:
G is hydroxymethylene or carbonyl;
$R_a$ and $R_b$ are each methyl or hydrogen;
$R_1$ is hydrogen or alkanoyl having one to five carbon atoms;
$R_2$ is hydrogen, bromo, chloro or fluoro;
$R_3$ is hydrogen, bromo, chloro, fluoro, alkyl having one to six carbon atoms, $(CH_2)_pCOOR_4$ wherein p is an integer from 0-6 and $R_4$ is hydrogen, methyl or ethyl, or $(CH_2)_qOH$ wherein q is an integer from 1-6; with the proviso that when $R_3$ is hydrogen or alkyl, $R_2$ is bromo, chloro or fluoro;
Z is $(-alk_1)_m-X-(alk_2)_n-$ wherein each of $(alk_1)$ and $(alk_2)$ has from 1 to 9 carbon atoms, with the proviso that the summation of carbon atoms in $(alk_1)$ plus $(alk_2)$ is not greater than 9;
m and n are each zero or 1;
X is oxygen or methylene; and
W is methyl, pyridyl, piperidyl or

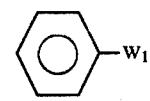

wherein $W_1$ is hydrogen, fluoro, chloro or methoxy.

An analgesically producing quantity of the compound when administered to a mammal produces analgesia therein.

11 Claims, No Drawings

SUBSTITUTED DIBENZO[B,D]PYRAN ANALGESICS

BACKGROUND OF THE INVENTION

This invention relates to hexahydropyran derivatives which are useful as CNS agents, especially as analgesics for treatment of mammals.

Analgesics which can control broad levels of pain with a minimum of side effects are being continually sought. Aspirin, the most commonly used analgesic agent, is of no practical value for the control of severe pain and is known to exhibit undesirable side effects. A number of other analgesics, such as d-propoxyphene, codeine and morphine, possess addictive liability. It is therefore desirable to discover compounds having improved and potent analgesic properties.

SUMMARY OF THE INVENTION

The present invention comprises novel compounds of formula

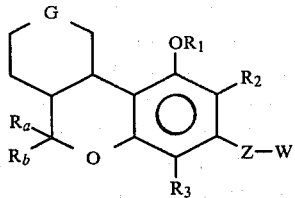

I or a pharmaceutically acceptable salt thereof wherein:
G is a hydroxymethylene or carbonyl;
$R_a$ and $R_b$ are each methyl or hydrogen;
$R_1$ is hydrogen or alkanoyl having one to five carbon atoms;
$R_2$ is hydrogen, bromo, chloro or fluoro;
$R_3$ is hydrogen, bromo, chloro, fluoro, alkyl having one to six carbon atoms, $(CH_2)_pCOOR_4$ wherein p is an integer from 0–6 and $R_4$ is hydrogen, methyl or ethyl, or $(CH_2)_qOH$ wherein q is an integer from 1–6; with the proviso that when $R_3$ is hydrogen, $R_2$ is bromo, chloro or fluoro;
Z is $(-alk_1)_m-X-(alk_2)_n$-wherein each of $(alk_1)$ and $(alk_2)$ has from 1 to 9 carbon atoms, with the proviso that the summation of carbon atoms in $(alk_1)$ plus $(alk_2)$ is not greater than 9;
m and n are each zero or 1;
X is oxygen or methylene; and
W is methyl, pyridyl, piperidyl or

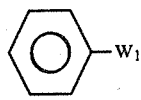

wherein $W_1$ is hydrogen, fluoro, chloro or methoxy.

Preferred compounds include those in which $R_2$ is hydrogen, G is hydroxymethylene or m is zero. Also preferred are compounds wherein m is zero, X is oxygen, $(alk_2)$ is 2-pentanyl and W is phenyl. Compounds wherein $R_2$ and $R_3$ are both bromo and wherein $R_2$ is bromo and $R_3$ is hydrogen are also preferred.

Additional preferred compounds are those in which $R_2$ is hydrogen and $R_3$ is either methyl or $(CH_2)_pCOOR_4$ wherein p is zero and $R_4$ is methyl.

Also included within the scope of the present invention are pharmaceutical compositions comprising a pharmaceutically acceptable carrier or diluent and an analgesic, tranquilizer, sedative, antianxiety, anticonvulsant, antidiarrheal or antiemetic effective amount of a novel compound described above. An analgesically producing quantity of the previously-discussed compound when administered to a mamml produces analgesia therein.

DETAILED DESCRIPTION

The compounds of this invention of formula I are readily prepared from the corresponding dl-6a beta,7,8,9,10,10a alpha-hexahydro-6-$R_a$,6-$R_b$-3-(Z—W)-6H-dibenzo[b,d]pyran-1,9-diol derivative (II), wherein G is hydroxymethyl, which can be prepared according to the procedure described in Bindra, U.S. Pat. No. 4,143,139, which is incorporated herein by reference. The 9-beta-ol derivative is shown. The numbering scheme employed is that shown for II. Although one sterochemisty is shown, other stero isomers are also included within the scope of the invention.

When G is carbonyl, a ketal can be formed to protect the carbonyl group during subsequent transformations. One method of ketalization is reacting the ketone with an alkyl alcohol, especially one having one to four carbon atoms, in the presence of an acid such as sulfuric acid, p-toluenesulfonic acid or hydrogen chloride under conditions which remove the by-product water. In one method an alcohol having a boiling point higher than water is employed and the water is distilled off. Alternatively, if an azeotrope forms between water and the alcohol, the azeotrope can be distilled off. Cyclic ketals can be formed using diols such as ethylene glycol as the starting alcohol. Another reaction method for ketal formation is the reaction of the ketone with an orthoformate ester in an alcohol solution where the alcohol corresponds to the alkoxy moiety of the orthoformate ester. Trimethyl orthoformate and methanol can be employed in this reaction with concentrated sulfuric acid, anhydrous hydrogen chloride or ammonium chloride as the acid catalyst.

When the ketal is no longer desired, it can be converted back to the ketone by known procedures such as treatment with aqueous acid at 10°–50° C., preferably about 25° C.

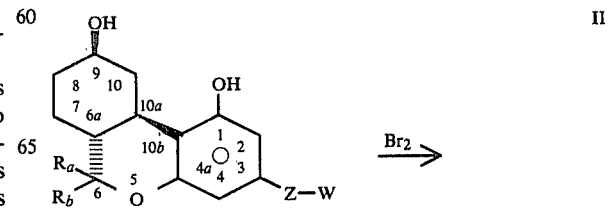

II

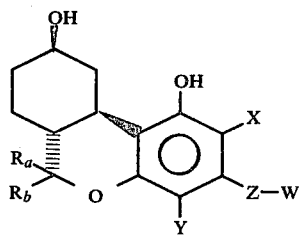

III

Halogenation of II results in III, X=Br, Cl, F, H; Y=Br, Cl, F, H, wherein at least one of X or Y is halogen. Bromination with bromine in a polar solvent system such as dichloromethane-tetrahydrofuran at a temperature range of −78° to 25° C., preferably about 0° C., leads to the bromination of II to form three isomers (X=H, Y=Br; X=Br, Y=H; X=Y=Br). Chlorination with chlorine in halogenated solvents such as carbon tetrachloride or dichloromethene at a temperature range of −78° to 25° C., preferably about 0° C., results in the preparation of chlorinated derivatives of III. Fluorination is carried out using a fluorinating agent such as 1-2% by volume of fluorine in nitrogen in halogenated solvents such as dichloromethene at −78° to 25° C., preferably about 0° C.

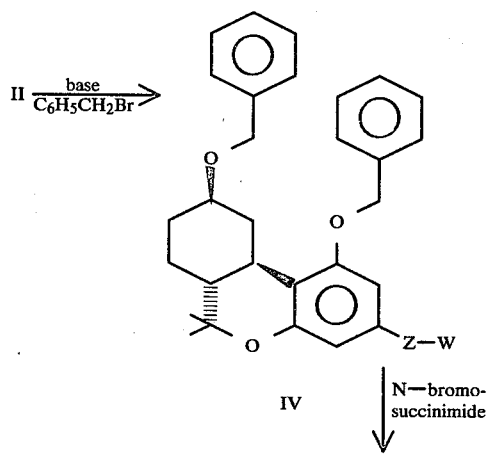

IV

↓ N—bromo-succinimide

VA + VB ⇐ Separate diastereomers

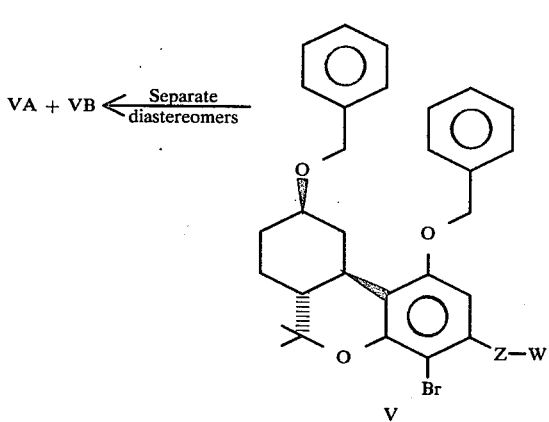

V

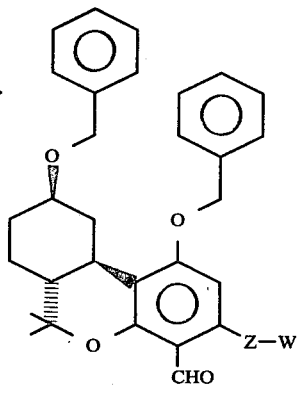

VA $\xrightarrow{\text{(1) n-C}_4\text{H}_9\text{Li}}_{\text{(2) (CH}_3\text{)}_2\text{NCHO}}$

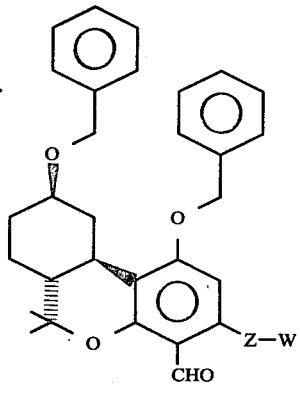

VI

Further reactions will be discussed for II wherein $R_a$ and $R_b$ are methyl is the starting material, although the corresponding starting compounds wherein $R_2$ is chloro, bromo or fluoro or wherein at least one of $R_a$ and $R_b$ is hydrogen, also undergo these reactions.

In order to carry out further tranformations on II, the hydroxyl groups at the 1- and 9-positions should be protected. A convenient procedure is to form the corresponding benzyl ethers as shown in formula IV. A strong base such as sodium hydride or sodium amide is reacted with II at a temperature range of about −10° to 50° C., preferably about 0° C. in a polar aprotic solvent such as dimethylformamide to form the dianion which is then reacted in situ with benzyl bromide or other benzyl derivative having a labile leaving group at a temperature range of about −10° to 50° C., preferably about 25° C. Other hydroxyl protecting groups such as methyl can also be employed.

The 4-position of IV can be selectively brominated using N-bromosuccinimde (NBS) in a nonpolar solvent such as carbon tetrachloride which does not interfere with bromination at a temperature range of −10° to 50° C., preferably about 0° C. to obtain V. The 4-position can be chlorinated by an analogous procedure using N-chlorosuccinimide. Alternatively, the hydroxyl groups of III (X=H, Y=Br) can be protected as benzyl ethers to also result in V.

The two diastereomers of V, denoted as A and B, can be separated by column chromatography, and are referred to as VA and VB. The remaining transformations while shown for VA could also be carried out for VB or for a mixture of the diastereomers.

The aldehyde VI is obtained by metal-halogen exchange of VA in an ether solvent such as tetrahydrofuran. At a temperature range of −100° to 25° C., preferably about −78° C., n-butyl lithium reacts by metal-halogen exchange with VA and the reaction product is in turn reacted with dimethylformamide at −100° to 25° C., preferably about −78° C., in situ, to obtain the desired aldehyde VI.

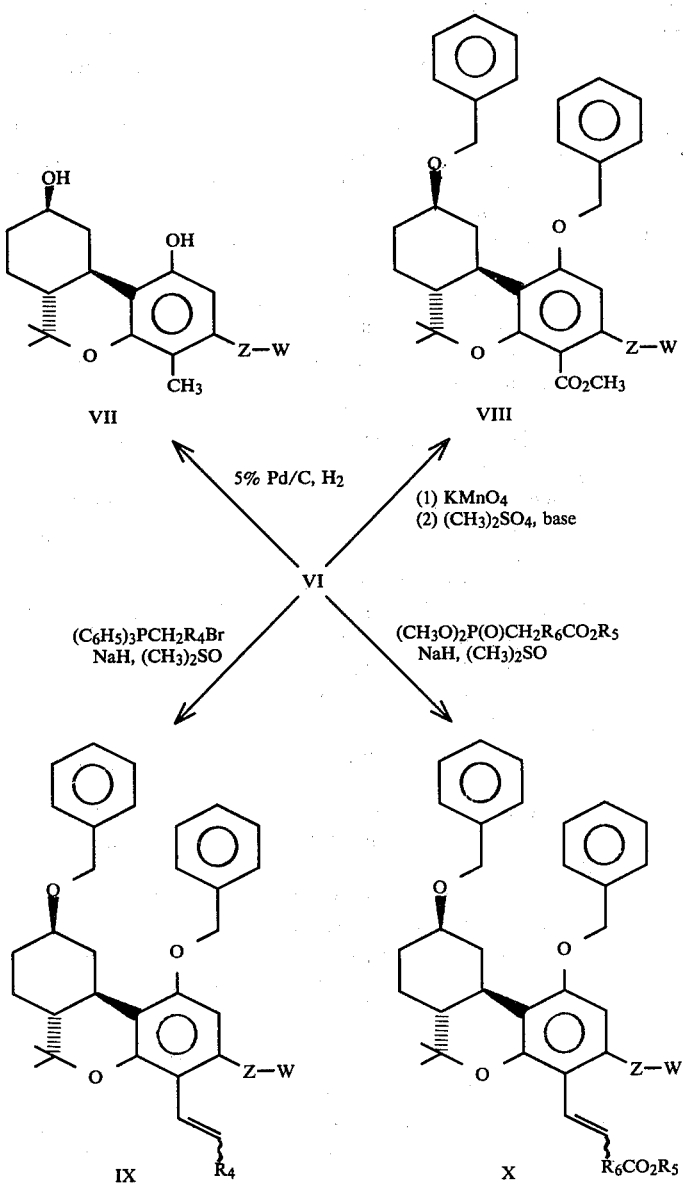

Hydrogenation of VI using 5% by weight of palladium on carbon removes the benzyl protecting groups and transforms the 4-carbonyl group to a methyl group to form VII. The hydrogenation is carried out in alcoholic solvents, such as a mixture of tetrahydrofuran and methanol, in which the compound to be hydrogenated is soluble, at a temperature range of 0°–50° C., preferably about 25° C. under, for example, 1 atm of hydrogen.

The aldehyde VI can be oxidized to form the corresponding acid which can then be alkylated to obtain the ester VIII. A suitable oxidizing agent is potassium permanganate in an aqueous solvent. Useful solvents include mixtures of alkyl ethers, lower alkyl ketones and water. The reaction is carried out at about 0°–100° C., preferably about 65° C.

The resulting acid can be alkylated by use of an alkylating agent and a strong base in a non-nucleophilic solvent. For example, the methyl ester (VIII) can be prepared with potassium carbonate and dimethyl sulfate in polar aprotic solvents such as 50% by volume acetonedioxane at a temperature of about 25°–100° C., preferably about 65° C. The benzyl protecting groups can be removed by means of the previously described hydrogenation procedure to obtain the methyl ester XI.

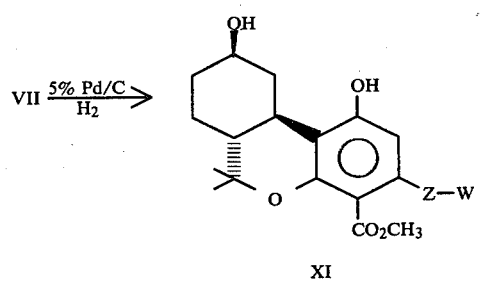

The aldehyde VI can participate in Wittig reactions to obtain alkene intermediates such as IX, wherein $R_4$ is an alkyl having one to four carbon atoms, and X, wherein $R_5$ is methyl or ethyl and $R_6$ is alkyl having zero to four carbon atoms. Either the corresponding triphenyl phosphonium salt such as the bromide or a dialkoxyphosphorylalkanoyloxyalkyl such as dimethyl phosphonoacetate is first reacted with a strong base such as sodium dimsylate in a polar aprotic solvent such as dimethylsulfoxide in the temperature range of 0°–70°C., preferably about 25° C. The resulting product is reacted in situ at 0°–70° C., preferably about 25° C. with the aldehyde VI in a polar aprotic solvent such as dimethylsulfoxide-tetrahydrofuran.

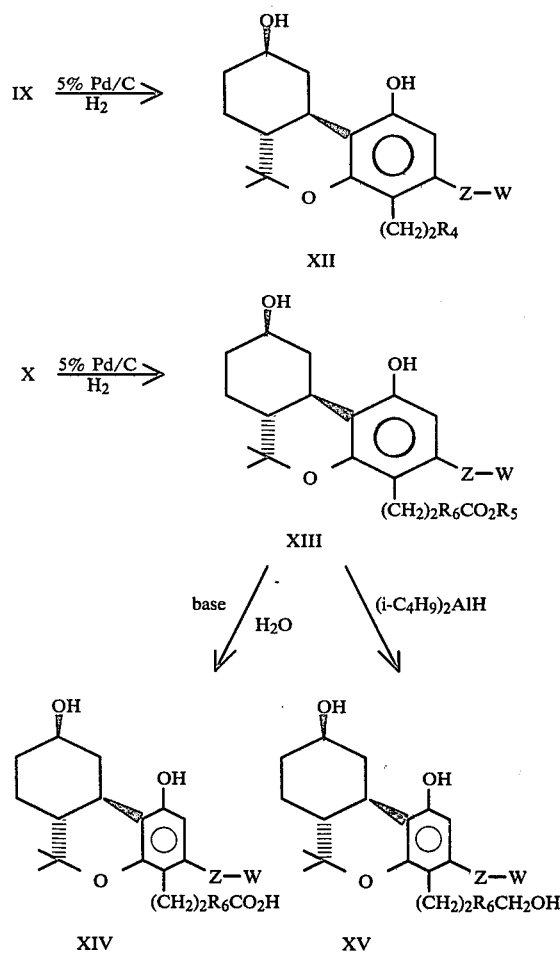

Olefins IX and X can be reduced at the same time their protecting benzyl groups are removed by means of the hydrogenation procedure previously described to obtain the corresponding alkyl XII and alkyl alkanoyloxy ester XIII compounds, respectively. The ester XIII can be hydrolyzed in base to obtain the corresponding alkylcarboxylic acid XIII. A large excess (e.g., about 6-fold) of an aqueous base such as sodium hydroxide or potassium hydroxide in a water-miscible solvent such as dioxane which also dissolves the ester XIII but which does not give rise to trans-esterification can be employed. The hydrolysis reaction is run in the temperature range of about 0°–100° C., preferably about 25° C.

The ester XIII can be reduced to the corresponding alcohol XV using a metal hydride reducing agent. While di-iso-butyl aluminum hydride is preferred other reducing agents such as lithium aluminum hydride may also be employed. The ester XIII can be dissolved in an ether such as tetrahydrofuran and the di-iso-butyl aluminum hydride can be dissolved in an aromatic solvent such as toluene. They are reacted at a temperature between about 0° and 50° C., preferably about 25° C.

Compounds of the formula I wherein $R_3$ is acetic acid are prepared by reacting IX, wherein $R_4$ is hydrogen, with borane in an ethereal solvent such as tetrahydrofuran at about −20° to 25° C., preferably about 0° C., followed by reaction with hydrogen peroxide in the presence of aqueous base such as sodium hydroxide or potassium hydroxide at −20° to 25° C., preferably about 0° C. The resulting hydroxyethyl derivative of IX ($R_3$ is 2-hydroxyethyl) is oxidized to the desired acetic acid derivative using an oxidizing reagent such as Jones' reagent (chromic anhydride in dilute aqueous sulfuric acid) in an alkyl ketone such as acetone at −20° to 25° C., preferably about 0° C. The hydroxyl-protecting benzyl groups can be removed by hydrogenation as previously described.

Compounds of formula I wherein W is p-methoxyphenyl are prepared according to the procedures of Bindra, U.S. Pat. No. 4,143,139. When X is methylene, the preparation of W-Z is generally as taught in the aforemention Bindra patent.

When $R_1$ is hydrogen, phenolic cationic salts can be formed. Pharmaceutically acceptable cations include lithium, sodium, potassium calcium, magnesium and the like.

If the phenolic ester of an alkyl carboxylic acid having 1–5 carbon atoms is desired, i.e., $R_1$ is alkanoyl having 1–5 carbon atoms, the phenol can be reacted with the corresponding acid anhydride with an acid acceptor such as 4-N-N-dimethylaminopyridine at −10° to 25° C., preferably about 0° C. Alternatively, the phenol can be reacted with the corresponding acid chloride in the presence of an acid acceptor such as sodium or potassium carbonate in an nonnucleophilic solvent to obtain the desired product (I, $R_1$=alkanoyl). The preferred alkanoyl has two carbon atoms.

The analgesic properties of the compounds of this invention are determined by tests using nociceptive stimuli.

TEST USING THERMAL NOCICEPTIVE STIMULI

Mouse Hot Plate Analgesic Testing

The method used is modified after Woolfe and MacDonald, *J. Pharmacol: Exp. Ther.*, 80, 300–307 (1944). A controlled heat stimulus is applied to the feet of mice on a ⅛ inch thick aluminum plate. A 250 watt reflector infrared heat lamp is placed under the bottom of the aluminum plate. A thermal regulator, connected to thermistors on the place surface, programs the heat lamp to maintain a constant temperature of 57° C. Each mouse is dropped into a glass cylinder (6½ inch diameter) resting on the hot plate, and timing is begun when the animal's feet touch the plate. The mouse is observed at 0.5 and 2 hours after treatment with the test compound for the first "flicking" movements of one or both hind feet, or until 10 seconds elapse without such movements. Morphine has an $MPE_{50}$=4–5.6 mg./kg.(s.c.).

TEST USING CHEMICAL NOCICEPTIVE STIMULI

Suppression of Phenylbenzoquinone Irritant-Induced Writhing

Groups of 45 Carworth Farms CF-1 mice are pretreated subcutaneously or orally with saline, morphine, codeine or the test compound. Twenty minutes (if treated subcutaneously) or fifty minutes (if treated orally) later, each group is treated with an intraperitoneal injection of phenylbenzoquinone, an irritant known to produce abdominal contractions. The mice are observed for 5 minutes for the presence or absence of writhing starting 5 minutes after the injection of the irritant. $MPE_{50}$'s of the drug pretreatments in blocking writhing are ascertained.

TEST USING PRESSURE NOCICEPTIVE STIMULI

Effect on the Haffner Tail Pinch Procedure

A modification of the procedure of Haffner, *Experimentelle Prufung Schmerzstillender. Deutch Med. Wschr.*, 55, 731–732 (1929) is used to ascertain the effects of the test compound on aggressive attacking responses elicited by a stimulus pinching the tail. Male albino rats (50–60 g.) of the Charles River (Sprague-Dawley) CD strain are used. Prior to drug treatment, and again at 0.5, 1, 2 and 3 hours after treatment, a Johns Hopkins 2.5 inch "bulldog" clamp is clamped onto the root of the rat's tail. The endpoint at each trial is clear attacking and biting behavior directed toward the offending stimulus, with the latency for attack recorded in seconds. The clamp is removed in 30 seconds if attacking has not yet occurred, and the latency of response is recorded as 30 seconds. Morphine is active at 17.8 mg./kg.(i.p.).

TEST USING ELECTRICAL NOCICEPTIVE STIMULI

The "Flinch-Jump" Test

A modification of the flinch-jump procedure of Tenen, *Psychopharmacologia*, 12, 278–285 (1968) is used for determining pain thresholds. Male albino rats (175–200 g.) of the Charles River (Sprague-Dawley) CD strain are used. Prior to receiving the drug, the feet of each rat are dipped into a 20% glycerol/saline solution. The animals are then placed in a chamber and presented with a series of 1-second shocks to the feet which are delivered in increasing intensity at 30 second intervals. These intensities are 0.26, 0.39, 0.52, 0.78, 1.05, 1.31, 1.58, 1.86, 2.13, 2.42, 2.72 and 3.04 mA. Each animal's behavior is rated for the presence of (a) flinch, (b) squeak and (c) jump or rapid forward movement at shock onset. Single upward series of shock intensities are presented to each rat just prior to, and at 0.5, 2, 4 and 24 hours subsequent to drug treatment.

Results of the above tests are recorded as percent maximum possible effect (%MPE). The %MPE of each group is statistically compared to the %MPE of the standard and the predrug control values. The %MPE is calculated as follows:

$$\% MPE = \frac{\text{test time} - \text{control time}}{\text{cutoff time} - \text{control time}} \times 100$$

The compounds of this invention, when used as analgesics via oral or parenteral administration, are conveniently administered in composition form. Such compositions include a pharmaceutical carrier selected on the basis of the chosen route of administration and standard pharmaceutical practices. For example, they can be administered in the form of tablets, pills, powders or granules containing such excipients as starch, milk sugar, certain types of clay, etc. They can be administered in capsules, in admixtures with the same or equivalent excipients. They can also be administered in the form of oral suspensions, solutions, emulsions, syrups and elixirs which may contain flavoring and coloring agents. For oral administration of the therapeutic agents of this invention, tablets or capsules containing from about 0.01 to about 100 mg. are suitable for most applications.

The physician will determine the dosage which will be most suitable for an individual patient and it will vary with the age, weight and response of the particular patient and the route of administration. Generally, however, the initial analgesic dosage in human adults weighing about 68 Kg may range from about 0.1 to about 750 mg. per day in single or divided doses. In many instances, it is not necessary to exceed 100 mg. daily. The favored oral dosage range is from about 1.0 to about 300 mg./day; the preferred dose is from about 1.0 to about 50 mg./day. The favored parenteral dose is from about 0.1 to about 100 mg./day; the preferred range from about 0.1 to about 20 mg./day.

This invention also provides pharmaceutical compositions, including unit dosage forms, valuable for the use of the herein described compounds as analgesics and other utilities disclosed herein. The dosage form can be given in single or multiple doses, as previously noted to achieve the daily dosage effective for a particular utility.

The compounds described herein can be formulated for administration in solid or liquid form for oral administration and in liquid form for parenteral administration. For example, capsules containing drugs of this invention can be prepared by mixing one part by weight of drug with nine parts of excipient such as starch or milk sugar and then loading the mixture into telescoping gelatin capsules such that each capsule contains 100 parts of the mixture. Tablets containing said compounds can be prepared, for example, by compounding suitable mixtures of drug and standard ingredients used in preparing tablets, and as starch, binders and lubricants, such that each tablet contains from about 0.10 mg. of drug per tablet.

Suspensions and solutions of these drugs are often prepared just prior to use and compositions suitable for such are generally dry solid compositions which are reconstituted for injectable administration.

The tranquilizer activity of the compounds of this invention is determined by orally administering them to rats at doses of from about 0.01 to about 50 mg./kg. of body weight and observing the subsequent decreases in spontaneous motor activity. The daily dosage range in mammals is from about 0.01 to about 100 mg.

Anticonvulsant activity is determined by subcutaneously administering the test compound to male Swiss mice (Charles River) weighing 14–24 g. in a suitable vehicle. The mice are used in groups of five. The day before use, the mice are fasted overnight but watered ad lib. Treatments are given at volumes of 10 ml. per kg. via a 25 gauge hypodermic needle. Subjects are treated with the test compound followed one hour later by challenge electroconvulsive shock, 50 mA. at 60 Hz. administered transcorneally. Controls are simultaneously run in which the mice are given only the vehicle as control treatment. The electroconvulsive shock treatment produces tonic extensor convulsions in all control mice with a latency of 1.5–3 seconds. Protection is recorded when a mouse exhibits no tonic extensor convulsions for 10 seconds after administration of electroconvulsive shock.

Antianxiety activity is determined in a manner similar to that for evaluating anticonvulsant activity except that the challenge convulsant is pentylenetetrazole, 120 mg./kg. administered intraperitoneally. This treatment produces chronic convulsions in less than one minute in over 95% of control mice treated. Protection is recorded when the latency to consulse is delayed at least 2-fold by a drug pretreatment.

Sedative/depressant activity is determined by treating groups of six mice subcutaneously with various doses of test agents. At 30 and 60 minutes post treatment, the mice are placed on a rotorod for one minute and evaluated for their performance on the rotorod. Inability of the mice to ride the rotorod is taken as evidence of sedative/depressant activity.

The antiemetic properties of the compounds of formula I can be determined in unanesthetized cats according to the procedure described in *Proceedings of the Society of Experimental Biology and Medicine*, volume 160, pages 437–40 (1979). The antidiarrheal utility can be determined by a modification of the procedure of Negimeers et al. *Modern Pharmacology-toxicology*, van Bever et al. Eds., volume 7, pages 68–73 (1976). In general the dosage levels and routes of administration for use of these compounds as antiemetic or antidiarrheal agents parallels those with respect to their use as analgesic agents.

The present invention will be illustrated by means of the following examples. It is to be understood, however, that the invention is not meant to be limited by the details described therein.

Infrared spectra (IR) were measured in chloroform (CHCl$_3$) solutions or as pressed potassium bromide discs (KBr disc) and diagnostic absorption bands are reported in wave numbers (cm$^{-1}$). Proton nuclear magnetic resonance spectra (PMR) were measured at 60 MHz for solutions in deutero-chloroform (CDCl$_3$) and peak positions are expressed in parts per million downfield from tetramethylsilane. The peak shapes are denoted as follows: s, singlet; d, doublet; t, triplet; q, quartet; m, multiplet; b, broad. Mass spectra (MS) or high resolution mass spectra (HRMS) are reported as positive ion mass per electron charge (m/e) with the parent ion denoted M+.

EXAMPLE 1 dl-6a beta,7,8,9,10,10a alpha-Hexahydro-4-bromo-6,6-dimethyl-3-[2-(5-phenylpentyloxy)]-6H-dibenzo[b,d]-pyran-1,9 beta-diol;

dl-6a beta,7,8,9,10,10a alpha-hexahydro-2-bromo-6,6-dimethyl-3-[2-(5-phenylpentyloxy)]-6H-dibenzo[b,d]-pyran-1,9 beta-diol;

dl-6a beta,7,8,9,10,10a alpha-hexahydro-2,4-dibromo-6,6-dimethyl-3-[2-(5-phenylpentyloxy)]-6H-dibenzo[b,d]-pyran-1,9 beta-diol To a −20° C. solution of 2.00 g (4.88 mmole) of dl-6a beta,7,8,9,10,10a alpha-hexahydro-6,6-dimethyl-3-[2-(5-phenylphentyloxy)]-6H-dibenzo[b,d]pyran-1,9 beta-diol in 17 ml dichloromethane and 17 ml tetrahydrofuran was added dropwise 4.88 ml of a 1M solution of bromine (4.88 mmole) in dichloromethane. After 5 minutes at −20° C. the reaction mixture was allowed to warm to 25° C. and then added to 100 ml saturated aqueous sodium bicarbonate. This mixture was extracted with 200 ml diethyl ether. The extract was washed with 100 ml saturated aqueous sodium bicarbonate, dried over anhydrous magnesium sulfate and evaporated to an oil. This oil was purified by column chromatography on 170 g silica gel eluted with 25% ethyl acetate-hexane to yield, in order of elution, 912 mg (38% yield) of the title 2-bromo compound as an oil, 102 mg (4.9% yield) of the title 2,4-dibromo compound as an oil and 511 mg (21% yield) of the title 4-bromo compound, m.p. 81°–3° C. (hexane).

Title 2-bromo compound:

PMR (CDCl$_3$): 1.03 (s, CH$_3$), 1.25 (d, J=6 Hz, CH$_3$), 1.37 (s, CH$_3$), 5.99 (s, aromatic H) and 7.19 (s, phenyl H) ppm.

IR (CHCl$_3$): 3448, 1607 and 1572 cm$^{-1}$.

HRMS: m/e 490.1569 (M+, Calcd for C$_{26}$H$_{33}$O$_4$Br: 490.1534), 488, 410, 344, 342 and 91.

Title 2,4-dibromo compound:

PMR (CDCl$_3$): 1.04 (s, CH$_3$), 1.23 (d, J=6 Hz, CH$_3$) 1.46 (s, CH$_3$) and 7.22 (s, phenyl H) ppm.

IR (CHCl$_3$): 3448, 1587 and 1547 cm$^{-1}$.

Title 4-bromo compound:

PMR (CDCl$_3$):1.02 (s, CH$_3$), 1.28 (d, J=6 Hz, CH$_3$), 1.42 (s, CH$_3$), 5.87 (s, aromatic H) and 7.20 (s, phenyl H) ppm.

IR (CHCl$_3$): 3268 and 1600 cm$^{-1}$.

HRMS: m/e 490.1595 (M+, Calcd for C$_{26}$H$_{33}$O$_4$Br: 490.1534), 488, 410, 344, 342, 217 and 91.

EXAMPLE 2 dl-6a beta,7,8,9,10,10a alpha-Hexahydro-3-[2-(5-phenylpentyloxy)]-4,6,6-trimethyl-6H-dibenzo[b,d]pyran-1,9 beta-diol, Diastereomer A A mixture of 500 mg (0.809 mmole) of dl-6a beta,7,8,9,10,10a alpha-hexahydro-1,9 beta-dibenzyloxy-6,6-dimethyl-3-[2-(5-phenylpentyloxy)]-6H-dibenzo[b,d]pyran-4-carboxaldehyde, diastereomer A, and 500 mg of 5% palladium on carbon and 50% water in 10 ml tetrahydrofuran and 5 ml methanol was stirred under 1 atm of hydrogen for 4 hours. The reaction was filtered through anhydrous magnesium sulfate and evaporated to an oil. The crude oil was purified by column chromatography on 16 g of silica gel eluted with 75% diethyl ether-hexane to yield in order of elution 265 mg (77% yield) of the title compound, m.p. 152°–153° C. (hexane) and 68 mg (19% yield) of dl-6a beta,7,8,9,10,10a alpha-hexahydro-6,6-dimethyl-4-hydroxymethyl-3-[2-(5-phenylpentyloxy)]-6H-dibenzo-[b,d]pyran-1,9 beta-diol, diastereomer A, as an oil.

PMR (CDCl$_3$): 0.99 (s,CH$_3$), 1.20 (d, J=6 Hz, CH$_3$), 1.32 (s, CH$_3$), 1.93 (s, CH$_3$), 5.78 (s, aromatic H) and 7.13 (bs, phenyl H) ppm.

IR (CHCl$_3$): 3546, 3278, 1608 and 1492 cm$^{-1}$.

HRMS: m/e 424.2591 (Calcd for C$_{27}$H$_{36}$O$_4$: 424.2604), 406, 278, 260 and 91.

EXAMPLE 3 dl-6a beta,7,8,9,10,10a alpha-Hexahydro-6,6-dimethyl-3-[2-(5-phenylpentyloxy)]-4-propyl-6H-dibenzo[b,d]pyran-1,9 beta-diol, Diastereomer A Using the hydrogenation procedure of Example 2, 506 mg (0.803 mmole) of dl-6a beta,7,8,9,10,10a alpha-hexahydro-1,9 beta-dibenzyloxy-6,6-dimethyl-3-[2-(5-phenylpentyloxy)]-4-(1-propenyl)-6H-dibenzo[b,d]pyran, diastereomer A, gave 182 mg (50% yield) of the title compound, m.p. 139°–141° C. (dichloromethane-pentane).

PMR (CDCl$_3$): 0.86 (t, J=7 Hz, CH$_3$), 1.00 (s, CH$_3$), 1.20 (d, J=6 Hz, CH$_3$), 1.36 (s, CH$_3$), 5.78 (s, aromatic H) and 7.17 (bs, phenyl H) ppm.

IR (CHCl$_3$): 3610, 3333, 1613 and 1493 cm$^{-1}$.

HRMS: m/e 452.2907 (M+, Calcd for C$_{29}$H$_{40}$O$_4$: 452.2916), 423, 306, 277, 259 and 91.

EXAMPLE 4 dl-6a beta,7,8,9,10,10a alpha-Hexahydro-6,6-dimethyl-4-pentyl-3-[2-(5-phenylpentyloxy)]-6H-dibenzo[b,d]pyran-1,9 beta-diol, Diastereomer A Using the hydrogenation procedure of Example 2, 614 mg (0.933 mmole) of dl-6a beta,7,8,9,10,10a alpha-hexahydro-1,9 beta-dibenzyloxy-6,6-dimethyl-4-(1-pentenyl)-3-[2-(5-phenylpentyloxy)]-6H-dibenzo[b,d]pyran, diastereomer A, gave 300 mg (67% yield) of the title compound, m.p. 149° C. (ether-hexane).

PMR (CDCl$_3$): 0.85 (m, CH$_3$), 1.00 (s, CH$_3$), 1.20 (d, J=6 Hz, CH$_3$), 1.32 (s, CH$_3$), 5.72 (s, aromatic H) and 7.16 (bs, phenyl H) ppm.

IR (CHCl$_3$): 3636, 3333 and 1613 cm$^{-1}$.

HRMS: m/e 480.3336 (M+, Calcd for C$_{31}$H$_{44}$O$_4$: 480.3228), 423, 334, 277, 259 and 91.

EXAMPLE 5 dl-6a beta,7,8,9,10,10a alpha-Hexahydro-4-(2-carbomethoxyethyl)-6,6-dimethyl-3-[2-(5-phenylpentyloxy)]-6H-dibenzo[b,d]pyran-1,9 beta-diol, Diastereomer A Using the hydrogenation procedure of Example 2, 689 mg (1.02 mmole) of dl-6a beta,7,8,9,10,10a alpha-hexahydro-E-4-(2-carbomethoxyethenyl)-1,9 beta-dibenzyloxy-6,6-dimethyl-3-[2-(5-phenylpentyloxy)]-6H-dibenzo[b,d]pyran, diastereomer A, gave 487 mg (96% yield) of the title compound, m.p. 86°–91° C. (hexane).

PMR (CDCl$_3$): 1.00 (s, CH$_3$), 1.22 (d, J=6 Hz, CH$_3$), 1.38 (s, CH$_3$), 3.66 (s, OCH$_3$), 5.81 (s, aromatic H) and 7.19 (bs, phenyl H) ppm.

IR (CHCl$_3$): 3588, 3358, 1728 and 1609 cm$^{-1}$.

MS: m/e 496 (M+), 423, 378, 350 and 91.

Analysis: Calcd for C$_{30}$H$_{40}$O$_6$: C, 72.55; H, 8.12. Found: C, 72.53; H, 7.97.

EXAMPLE 6 dl-6a beta,7,8,9,10,10a alpha-Hexahydro-4-(2-carboxyethyl)-6,6-dimethyl-3-[2-(5-phenylpentyloxy)]-6H-dibenzo[b,d]pyran-1,9 beta-diol, Diastereomer A A mixture of 100 mg (0.202 mmole) of dl-6a beta,7,8,9,10,10a alpha-hexahydro-4-(2-carbomethoxyethyl)-6,6-dimethyl-3-[2-(5-phenylpentyloxy)]-6H-dibenzo[b,d]pyran-1,9 beta-diol, diastereomer A, and 2 ml 6N aqueous sodium hydroxide was heated at reflux for 40 minutes in 2 ml dioxane. The reaction mixture was cooled and added to 200 ml diethyl ether—50 ml 1N aqueous hydrochloric acid—50 ml saturated aqueous sodium chloride. The organic extract was dried over anhydrous magnesium sulfate and evaporated. The residue was crystallized from diethyl ether-pentane to give 91 mg (94% yield) of the title compound, m.p. 160° C.

IR (KBr disc): 3402, 3000 (broad), 1708, 1612 and 1599 cm$^{-1}$.

HRMS: m/e 482.2633 (M+, Calcd for C$_{29}$H$_{38}$O$_6$: 482.2658), 336, 277 and 91.

EXAMPLE 7 dl-6a beta,7,8,9,10,10a alpha-Hexahydro-6,6-dimethyl-4-(3-hydroxypropyl)-3-[2-(5-phenylpentyloxy)]-6H-dibenzo[b,d]pyran-1,9 beta-diol, Diastereomer A To a 25° C. solution of 250 mg (0.504 mmole) of dl-6a beta,7,8,9,10,10a alpha-hexahydro-4-(2-carbomethoxyethyl)-6,6-dimethyl-3-[2-(5-phenylpentyloxy)]-6H-dibenzo[b,d]pyran-1,9 beta-diol in 10 ml tetrahydrofuran was added 2.11 ml of 1M diisobutylaluminumhydride in toluene. The reaction mixture was stirred 1 hour at 25° C. and then added to 100 ml 1N aqueous hydrochloric acid. The quenched reaction mixture was extracted with two 100 ml portions of diethyl ether. The ether extract was washed with 100 ml saturated aqueous sodium chloride, dried over anhydrous magnesium sulfate and evaporated to an oil. This oil was crystallized in ethyl acetate-hexane to give 174 mg (74% yield) of the title compound, m.p. 170°–171° C.

PMR (CDCl$_3$): 1.02 (s, CH$_3$), 1.29 (d, J=6 Hz, CH$_3$), 1.39 (s, CH$_3$), 6.02 (s, aromatic H) and 7.18 (bs, phenyl H) ppm.

IR (KBr disc): 3373 (broad) and 1605 cm$^{-1}$.

MS: m/e 468 (M+), 300, 279, 247 and 219.

EXAMPLE 8 dl-6a beta,7,8,9,10,10a alpha-Hexahydro-4-carbomethoxy-6,6-dimethyl-3-[2-(5-phenylpentyloxy)]-6H-dibenzo[b,d]pyran-1,9 beta-diol, Diastereomer A Using the procedure of Example 1, 380 mg (0.588 mmole) of dl-6a beta,7,8,9,10,10a alpha-hexahydro-4-carbomethoxy-1,9 beta-dibenzyloxy-6,6-dimethyl-3-[2-(5-phenylpentyloxy)]-6H-dibenzo[b,d]pyran, diastereomer A, gave 240 mg (87% yield) of the title compound, m.p. 174°–176° C.

PMR (CDCl$_3$): 1.00 (s, CH$_3$), 1.21 (d, J=6 Hz, CH$_3$), 1.32 (s, CH$_3$), 3.80 (s, OCH$_3$), 5.82 (s, aromatic H) and 7.18 (bs, phenyl H) ppm.

IR (CHCL$_3$): 3590, 3303, 1723 and 1604 cm$^{-1}$.

HRMS: m/e 468.2577 (M+, Calcd for C$_{28}$H$_{36}$O$_6$: 468.2502), 437, 322, 290, 272, 257 and 91.

Analysis: Calcd. for C$_{28}$H$_{36}$O$_6$: C, 71.77; H, 7.74. Found: C, 71.57; H, 7.37.

EXAMPLE 9

The previously described chemical nociceptive stimuli test employing suppression of phenylbenzoquinone irritant-induced writhing was performed. The title compounds of Examples 1 (2-bromo compound and 4-bromo compound) and 3, when administered subcutaneously, each has an MPE$_{50}$ of less than about 10 mg/kg. The title compounds of Examples 3, 4, 5 and 6 when administered subcutaneously, each had an MPE$_{50}$ of about 56 mg/kg. The title compounds of Examples 1 (2,4-dibromo compound), 7 and 8, when administered orally, each has an MPE$_{50}$ of greater than about 56 mg/kg. The title compound of Example 8, when administered orally had a MPE$_{50}$ of about 56 mg/kg.

Preparation A dl-6a beta,7,8,9,10,10a alpha-Hexahydro-1,9 beta-dibenzyloxy-6,6-dimethyl-3-[2-(5-phenylpentyloxy)]-6H-dibenzo[b,d]pyran To a 0° slurry of 766 mg (31.9 mmole) of sodium hydride in 14 ml dimethylformamide was added dropwise a solution of 5.45 g (13.3 mmole) of dl-6a beta,7,8,9,10,10a alpha-hexahydro-6,6-dimethyl-3-[2-(5-phenylpentyloxy)]-6H-dibenzo[b,d]pyran-1,9 beta-diol (prepared according to Bindra, U.S. Pat. No. 4,243,674) in 14 ml dimethylformamide. The reaction was allowed to warm to 25° C., stirred 15 minutes longer and then 3.32 ml (27.9 mmole) of benzyl bromide was added. After stirring 3 days at 25°, 0.8 ml of benzyl bromide was added to the reaction mixture. After stirring an additional 4 days at 25°, 191 mg of sodium hydride and 0.83 ml of benzyl bromide were added to the reaction. After stirring 5 more days at 25° C. the reaction mixture was added to 1 liter saturated aqueous sodium chloride and extracted with 300 ml diethyl ether. The ether extract was washed with 100 ml saturated aqueous sodium chloride, dried over anhydrous magnesium sulfate and evaporated to an oil. This oil was purified by column chromatography on 325 g of silica gel eluted with 10% diethyl ether-hexane to yield 6.20 (77% yield) of the title compound as an oil.

PMR (CDCl$_3$): 1.07 (s, CH$_3$), 1.28 (d, J=6 Hz, CH$_3$), 1.38 (s, CH$_3$), 4.35 (ab doublet, —OCH$_2$—), 4.98 (s, —OCH$_2$—), 6.00 (d, J=2 Hz, aromatic H), 6.12 (d, J=2 Hz, aromatic H) and 7.1–7.5 (m, phenyl H) ppm.

Preparation B dl-6a beta,7,8,9,10,10a alpha-Hexahydro-4-bromo-1,9 beta-dibenzyloxy-6,6-dimethyl-3-[2-(5-phenylpentyloxy)]-6H-dibenzo[b,d]pyran To a 0° C. solution of 39.3 g (66.6 mmole) of dl-6a beta,7,8,9,10,10a alpha-hexahydro-1,9 beta-dibenzyloxy-6,6-dimethyl-3-[2-(5-phenylpentyloxy)]-6H-dibenzo[b,d]pyran in 240 ml carbon tetrachloride was added 11.9 g (66.6 mmole) of N-bromosuccinimide. The reaction was stirred 2 hours at 0° C. and then allowed to warm to 25° C. over 12 hours. The reaction was filtered to remove succinimide and evaporated to an oil. This oil was purified by column chromatography on 1.35 kg of silica gel eluted with 20-55% dichloromethane-hexane to yield in order of elution 12.0 g (27% yield) of diastereomer A, m.p. 129°–132° C. (hexane), 10.8 (24% yield) mixture of diastereomer A and B and 17.1 g (38% yield) of diastereomer B, m.p. 132°–133° C.

Diastereomer A:

PMR (CDCL$_3$): 1.02 (s, CH$_3$), 1.29 (d, J=6 Hz, CH$_3$), 1.42 (s, CH$_3$), 4.35 (ab doublet, —OCH$_2$—) 4.98 (s, —OCH$_2$—), 6.10 (s, aromatic H), 7.16, 7.21 and 7.34 (bs, phenyl H) ppm.

IR (CHCl$_3$): 1600 and 1565 cm$^{-1}$.

Analysis: Calcd for C$_{40}$H$_{45}$O$_4$Br: C, 71.74; H, 6.78. Found: C, 71.74; H, 6.86.

Diastereomer B:

PMR (CDCl$_3$): 1.04 (s, CH$_3$), 1.29 (d, J=6 Hz, CH$_3$), 1.47 (s, CH$_3$), 4.40 (ab doublet, —OCH$_2$—), 5.01 (s, —OCH$_2$—), 6.18 (s, aromatic H), 7.23, 7.30 and 7.41 (bs, phenyl H) ppm.

IR (CHCl$_3$): 1600 and 1565 cm$^{-1}$.

Analysis: Calcd for C$_{40}$H$_{45}$O$_4$Br: C, 71.74; H, 6.78; Br, 11.93. Found: C, 71.57; H, 6.45; Br, 12.29.

Preparation C dl-6a beta,7,8,9,10,10a alpha-Hexahydro-1,9 beta-dibenzyloxy-6,6-dimethyl-3-[2-(5-phenylpentyloxy)]-6H-dibenzo[b,d]pyran-4-carboxaldehyde, Diastereomer A To a −78° C. solution of 3.32 g (4.96 mmole) of dl-6a beta,7,8,9,10,10a alpha-hexahydro-4-bromo-1,9 beta-dibenzyloxy-6,6-dimethyl-3-[2-(5-phenylpentyloxy)]-6H-dibenzo[b,d]pyran, diastereomer A in 17 ml of tetrahydrofuran was added dropwise 2.16 ml of 2.3M n-butyllithium in hexane. The reaction mixture was stirred 1 hour at −78° and then 0.76 ml (9.81 mmole) of dimethylformamide was added dropwise. The reaction mixture was stirred 10 minutes longer at −78° C. and then allowed to warm to 25° C. The reaction mixture was quenched by addition to 250 ml saturated aqueous sodium chloride and extracted with three 75 ml portions of dichloromethane. The combined organic extract was washed with three 100 ml portions of saturated aqueous sodium chloride, dried over anhydrous magnesium sulfate and evaporated. The residue was crystallized in diethyl ether-dichloromethane to yield 2.40 g (78% yield) of the title compound, m.p. 142° C.

PMR (CDCl$_3$): 1.04 (s, CH$_3$), 1.27 (d, J=6 Hz, CH$_3$), 1.42 (s, CH$_3$), 4.33 (ab doublet, —OCH$_2$—), 5.02 (s, —OCH$_2$—), 6.01 (s, aromatic H), 7.20, 7.25 and 7.40 (bs, phenyl H) and 10.33 (s, CHO) ppm.

IR (CHCl$_3$): 1666, 1587 and 1562 cm$^{-1}$.

HRMS: m/e 618.3333 (M+, Calcd. for C$_{41}$H$_{46}$O$_5$: 618.3333), 472, 275, 274, 273 and 91.

Preparation D dl-6a beta,7,8,9,10,10a alpha-Hexahydro-1,9 beta-dibenzyloxy-6,6-dimethyl-3-[2-(5-phenylpentyloxy)]-4-(1-propenyl)-6H-dibenzo[b,d]pyran, Diastereomer A To a cooled 10° C. solution of dimsyl sodium (1.89 mmole) in 1 ml dimethyl sulfoxide was added a solution of 703 mg (1.89 mmole) of ethyltriphenylphosphonium bromide in 1.6 ml dimethylsulfoxide. The reaction mixture was stirred 10 minutes longer and then a solution of 585 mg (0.947 mmole) of dl-6a beta-7,8,9,10,10a alpha-hexahydro-1,9 beta-dibenzyloxy-6,6-dimethyl-3-[2-(5-phenylpentyloxy)]-6H-dibenzo[b,d]pyran-4-carboxaldehyde, diastereomer A, in 2 ml dimethylsulfoxide and 2 ml tetrahydrofuran was added dropwise. The reaction mixture was stirred for 20 minutes at 25° C. and then added to 250 ml saturated aqueous sodium chloride and extracted with 300 ml diethyl ether. The ether extract was washed with three 100 ml portions of saturated aqueous sodium chloride and dried over anhydrous magnesium sulfate, followed by solvent evaporation. Triphenylphosphine oxide was removed by crystallization from diethyl ether-pentane. The residue was purified by column chromatography on 50 g of silica gel eluted with 10% diethyl ether-hexane to yield 516 mg (86% yield) of the title compound as an oil.

PMR (CDCl$_3$): 1.02 (s, CH$_3$), 1.23 (d, J=6 Hz, CH$_3$), 1.40 (s, CH$_3$), 1.9 (m, CH$_3$), 4.33 (ab doublet, —OCH$_2$—), 4.99 (s, —OCH$_2$—), 6.13 (s, aromatic H), 6.57 (m, vinyl H) and 7.1–7.5 (m, phenyl and vinyl H) ppm.

IR(CHCl₃): 1626, 1542 and 1562 cm⁻¹.

Preparation E dl-6a beta,7,8,9,10,10a alpha-Hexahydro-1,9 beta-dibenzyloxy-6,6-dimethyl-4-(1-pentenyl)-3-[2-(5-phenylpentyloxy)]-6H-dibenzo[b,d]pyran, Diastereomer A Using the procedure of Preparation D, 600 mg (0.97 mmole) dl-6a beta,7,8,9,10,10a alpha-hexahydro-1,9 beta-dibenzyloxy-6,6-dimethyl-3-[2-(5-phenylpentyloxy)]-6H-dibenzo[b,d]pyran-4-carboxaldehyde, diastereomer A and 775 mg (1.94 mmole) of n-butyltriphenylphosphonium bromide gave a quantitative yield of the title compound as an oil.

PMR (CDCl₃): 0.98 (m, CH₃), 1.02 (s, CH₃), 1.25 (d, J=6 Hz, CH₃), 1.41 (s, CH₃), 4.35 (ab doublet, —OCH₂—), 4.98 (s, —OCH₂—), 6.07 (s, aromatic H), 6.53 (m, vinyl H) and 7.1–7.5 (m, phenyl and vinyl H) ppm.

IR (CHCl₃): 1597 and 1575 cm⁻¹.

Preparation F dl-6a beta,7,8,9,10,10a alpha-Hexahydro-E-4-(2-carbomethoxyethenyl)-1,9 beta-dibenzyloxy-6,6-dimethyl-3-[2-(5-phenylpentyloxy)]-6H-dibenzo[b,d]pyran, Diastereomer A Using the procedure of Preparation D, 700 mg (1.13 mmole) dl-6a beta,7,8,9,10,10a alpha-hexahydro-1,9 beta-dibenzyloxy-6,6-dimethyl-3-[2-(5-phenylpentyloxy)]-6H-dibenzo[b,d]pyran-4-carboxaldehyde, diastereomer A, and 247 mg (1.36 mmole) trimethyl phosphonoacetate gave 697 mg (92% yield) of the title compound as an oil.

PMR (CDCl₃): 1.10 (s, CH₃), 1.33 (d, J=6 Hz, CH₃), 1.51 (s, CH₃), 3.78 (s, OCH₃), 4.38 (ab doublet, —OCH₂—), 5.01 (s, —OCH₂—), 6.07 (s, aromatic H), 6.79 (d, J=16 Hz, vinyl H), 7.2, 7.22 and 7.37 (bs, phenyl H) and 8.10 (d, J=16 Hz, vinyl H) ppm.

IR (CHCl₃): 1683, 1608, 1582 and 1562 cm⁻¹.

Preparation G dl-6a beta,7,8,9,10,10a alpha-Hexahydro-4-carbomethoxy-1,9 beta-dibenzyloxy-6,6-dimethyl-3-[2-(5-phenylpentyloxy)]-6H-dibenzo[b,d]pyran, Diastereomer A To a 65° C. solution of 1.50 g (2.43 mmole) dl-6a beta,7,8,9,10,10a alpha-hexahydro-1,9 beta-dibenzyloxy-6,6-dimethyl-3-[2-(5-phenylpentyloxy)]-6H-dibenzo[b,d]pyran-4-carboxaldehyde, diastereomer A, in 15 ml dioxane—15 ml acetone—2 ml water was added 2.6 g (16.5 mmole) of potassium permanganate over a period of 1.5 hours. The cooled reaction mixture was filtered through Supercel with 50% acetone-dioxane. The filtrate was heated to 65° C. with 375 mg potassium carbonate and then 0.229 ml (2.42 mmole) of dimethyl sulfate was added. The reaction mixture was stirred 30 minutes and then evaporated in vacuo. The residue was extracted with ethyl acetate and the extract dried over anhydrous magnesium sulfate, followed by solvent evaporation. The crude product was purified by column chromatography on 100 g silica gel eluted with 15% ethyl acetate-hexane to give 631 mg (40% yield) of the title compound, m.p. 82°–84° C. (hexane).

PMR (CDCl₃): 1.00 (s, CH₃), 1.23 (d, J=6 Hz, CH₃), 1.31 (s, CH₃), 3.76 (s, OCH₃), 4.33 (ab doublet, —OCH₂—), 4.96 (s, —OCH₂—), 6.01 (s, aromatic H), 7.15, 7.20 and 7.31 (bs, phenyl H).

IR (CHCl₃): 1726 and 1601 cm⁻¹.

Preparation H dl-6a beta,7,8,9,10,10a alpha-Hexahydro-1,9 beta-dibenzyloxy-6,6-dimethyl-4-(2-hydroxyethyl)-3-[2-(5-phenylpentyloxy)]-6H-dibenzo[b,d]pyran To a 0° solution of 1.00 g (1.62 mmole) of dl-6a beta,7,8,9,10,10a alpha-hexahydro-1,9 beta-dibenzyloxy-6,6-dimethyl-4-ethenyl-3-[2-(5-phenylpentyloxy)]-6H-dibenzo [b,d]pyran (which is prepared according to Preparation D employing methyltriphenylphosphonium bromide) in 10 ml tetrahydrofuran is slowly added 1 ml of a 1M solution of borane-tetrahydrofuran in tetrahydrofuran. After stirring 1 hr, 2 ml of 6N sodium hydroxide are added followed by 0.5 ml of 30% by volume aqueous hydrogen peroxide. The reaction is stirred 30 minutes longer and then added to 200 ml ether —200 ml saturated aqueous sodium chloride. The organic extract is dried over anhydrous magnesium sulfate and evaporated to yield the title compound.

Preparation I dl-6a beta,7,8,9,10,10a alpha-Hexahydro-1,9 beta-dibenzyloxy-4-carboxymethyl-6,6-dimethyl-3-[2-(5-phenylpentyloxy)]-6H-dibenzo[b,d]pyran To a 0° solution of 1.00 g (1.58 mmole) of dl-6a beta,7,8,9,10,10a alpha-hexahydro-1,9 beta-dibenzyloxy-6,6-dimethyl-4-(2-hydroxyethyl)-3-[2-(5-phenylpentyloxy)]-6H-dibenzo[b,d]pyran in 10 ml of acetone is slowly added 0.84 ml (2.08 mmole) of Jones' reagent. The reaction is stirred 0.5 hr longer and then added to 150 ml water-200 ml ether. The organic extract is dried over magnesium sulfate and evaporated to yield the title compound.

We claim:

1. A compound of the formula

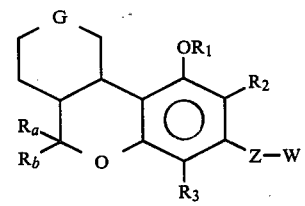

or a pharmaceutically acceptable salt thereof wherein:
G is hydroxymethylene or carbonyl;
$R_a$ and $R_b$ are each methyl or hydrogen;
$R_1$ is hydrogen or alkanoyl having one to five carbon atoms;
$R_2$ is hydrogen, bromo, chloro or fluoro;
$R_3$ is hydrogen, bromo, chloro, fluoro, alkyl having one to six carbon atoms, $(CH_2)_p COOR_4$ wherein p is an integer from 0–6 and $R_4$ is hydrogen, methyl or ethyl, or $(CH_2)_q OH$ wherein q is an integer from 1–6; with the proviso that when $R_3$ is hydrogen or alkyl, $R_2$ is bromo, chloro or fluoro;
Z is —(alk₁)$_m$—X—(alk₂)$_n$— wherein each of (alk₁) and (alk₂) has from 1 to 9 carbon atoms, with the proviso that the summation of carbon atoms in (alk₁) plus (alk₂) is not greater than 9;
m and n are each zero or 1;
X is oxygen or methylene; and W is methyl, pyridyl, piperidyl or

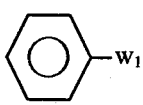

wherein $W_1$ is hydrogen, fluoro, chloro or methoxy.

2. A compound according to claim 1 wherein $R_2$ is hydrogen.

3. A compound according to claim 1 wherein m is zero.

4. A compound according to claim 3 wherein X is oxygen, $(alk_2)$ is 2-pentanyl and W is phenyl.

5. A compound according to claim 1 or claim 4 wherein $R_2$ and $R_3$ are both bromo.

6. A compound according to claim 1 or claim 4 wherein $R_2$ is bromo, and $R_3$ is hydrogen.

7. A compound according to claim 4 wherein $R_2$ is hydrogen.

8. A compound according to claim 1 or claim 4 wherein $R_2$ is hydrogen and $R_3$ is $(CH_2)_p COOR_4$ wherein p is zero and $R_4$ is methyl.

9. A compound according to claim 1 or claim 4 wherein G is hydroxymethylene.

10. A pharmaceutical composition comprising a pharmaceutically acceptable carrier or diluent and an analgesic, tranquilizer, sedative, antianxiety, anticonvulsant, antidiarrheal or antiemetic effective amount of a compound of claim 1.

11. A method for producing analgesia in a mammal which comprises administering thereto an analgesic producing quantity of a compound of claim 1.

* * * * *